(12) United States Patent
Sinha (10) Patent No.: US 8,176,783 B2
(45) Date of Patent: May 15, 2012

(54) NON-CONTACT FLUID CHARACTERIZATION IN CONTAINERS USING ULTRASONIC WAVES (75) Inventor: Dipen N. Sinha, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/861,208

(22) Filed: Sep. 25, 2007

(65) Prior Publication Data

US 2009/0078050 A1 Mar. 26, 2009

(51) Int. Cl.
*G01N 29/02* (2006.01)
*G01N 29/22* (2006.01)

(52) U.S. Cl. ............ 73/579; 73/597; 73/599; 73/602; 73/643

(58) Field of Classification Search .......... 73/579, 73/290 V, 643, 596–600, 602
See application file for complete search history.

(56) References Cited

U.S. PATENT DOCUMENTS

| | | | | |
|---|---|---|---|---|
| 5,012,428 A | * | 4/1991 | Ueno et al. | 700/280 |
| 5,255,564 A | * | 10/1993 | Glad et al. | 73/597 |
| 5,359,541 A | * | 10/1994 | Pope et al. | 702/25 |
| 5,767,407 A | * | 6/1998 | Sinha | 73/579 |
| 5,804,728 A | * | 9/1998 | Beall et al. | 73/598 |
| 5,824,908 A | * | 10/1998 | Schindel et al. | 73/632 |
| 5,886,262 A | * | 3/1999 | Sinha | 73/579 |
| 5,919,144 A | * | 7/1999 | Bridger et al. | 600/561 |
| 6,186,004 B1 | * | 2/2001 | Kaduchak et al. | 73/596 |
| 6,234,023 B1 | * | 5/2001 | Collins et al. | 73/597 |
| 6,250,159 B1 | * | 6/2001 | Kreier et al. | 73/602 |
| 6,275,781 B1 | * | 8/2001 | Maness et al. | 702/182 |
| 6,363,788 B1 | * | 4/2002 | Gorman et al. | 73/597 |
| 6,644,119 B1 | * | 11/2003 | Sinha | 73/579 |
| 6,840,108 B2 | * | 1/2005 | Stauffer | 73/630 |
| 6,890,302 B2 | * | 5/2005 | Oravecz et al. | 600/443 |
| 6,959,602 B2 | * | 11/2005 | Peterson et al. | 73/602 |
| 7,010,979 B2 | * | 3/2006 | Scott | 73/596 |
| 7,353,709 B2 | * | 4/2008 | Kruger et al. | 73/599 |
| 2002/0112540 A1 | * | 8/2002 | Zeroug et al. | 73/579 |
| 2009/0078049 A1 | * | 3/2009 | Sinha | 73/623 |

* cited by examiner

*Primary Examiner* — Helen C. Kwok
(74) *Attorney, Agent, or Firm* — Samuel M. Freund; Cochran Freund & Young LLC; Meredith H. Schoenfeld (57) ABSTRACT

Apparatus and method for non-contact (stand-off) ultrasonic determination of certain characteristics of fluids in containers or pipes are described. A combination of swept frequency acoustic interferometry (SFAI), wide-bandwidth, air-coupled acoustic transducers, narrowband frequency data acquisition, and data conversion from the frequency domain to the time domain, if required, permits meaningful information to be extracted from such fluids.

9 Claims, 6 Drawing Sheets

NON-CONTACT FLUID CHARACTERIZATION IN CONTAINERS USING ULTRASONIC WAVES

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to identification and monitoring of substances and, more particularly, to non-invasive, non-contact identification and monitoring of substances using ultrasonic waves.

BACKGROUND OF THE INVENTION

Existing methods for identifying chemicals (fluids) involve various kinds of spectroscopy, chromatography and standard chemical analyses. Such methods are not applicable when the chemicals are located inside of sealed containers and analysis must be performed noninvasively. An example would be identifying chemical warfare agents inside munitions or other toxic liquids in various containers. In such situations, it is imperative that the investigators not be exposed to chemical hazards and that the integrity of the container is not affected by the measurements. Other situations include monitoring of industrial chemicals flowing through pipes or very clean pharmaceutical products kept in reaction vessels. In such situations, it is often desirable that the pipe or vessel is not penetrated.

In U.S. Pat. No. 5,767,407 for "Noninvasive Identification Of Fluids By Swept-Frequency Acoustic Interferometry" which issued to Dipen N. Sinha on Jun. 16, 1998, a method for rapid, noninvasive identification and monitoring of chemicals in sealed containers or containers where direct access to the chemical is not possible is described. External transducers introduce standing-wave ultrasonic vibrational pattern into a fluid enclosed in a container over a range of frequencies. Multiple ultrasonic acoustic properties (up to four) of a fluid are simultaneously determined. For example, the speed of sound, sound attenuation, the liquid density, and the frequency dependence of sound absorption in the liquid, or a subset of these, may be determined from which chemical compounds can be identified. When the acoustic transducers cannot be placed directly in contact with the fluid, the transducers may be placed on the outside of the container wall.

The swept frequency acoustic interferometry (SFAI) technique for fluid characterization requires physical contact between the acoustic transducers and the container or pipe wall which limits the value of the technique in situations where direct physical contact is neither possible nor desirable. For example, in bottling plants where high speed measurements are required, placing coupling gels on each bottle is prohibitive. Further, in situations where the container surface is contaminated, hot or radioactive, direct contact is not indicated. It is possible, in principle, to make non-contact measurements using electromagnetic acoustic transducers, but these only operate in nonmagnetic metallic containers and must have sufficient wall thickness for the generation of the sound waves.

Additionally, whenever a transducer is attached to a measurement system, the transducer itself may affect the measurement since the presence of a solid transducer attached to the wall of a container essentially provides a leakage path for sound that otherwise would bounce back and forth within the container. As examples, this leakage depends on the contact pressure of the transducer and the coupling gel used, and is difficult to quantify. Subtraction of the effect of the transducers has been reported. Each time the sound inside the container reaches the inside wall of a container, it now finds an alternate path to travel through the wall to the solid transducer instead of being reflected and slowly decaying due to losses by absorption in the liquid. It is this sound absorption in the liquid that is of relevance to measure.

In U.S. Pat. No. 6,186,004 for "Apparatus And Method For Remote, Noninvasive Characterization Of Structures And Fluids Inside Containers" which issued to Gregory Kaduchack et al. on Feb. 13, 2001, an apparatus and method for remote, non-contact evaluation of structures and containers at large distances (on the order of several meters) in air is described. The invention utilizes an air-coupled, parametric acoustic array to excite resonance vibrations of elastic, fluid-filled vessels and structural members (at frequencies less than 40 kHz), where a nonlinear mixing process in the air medium transforms highly directional, narrow beamwidth higher acoustic frequencies into lower acoustic frequencies suitable for vibrational excitation of common structures. Vibrations were readily detected using a laser vibrometer in a fixed position relative to the acoustic array. Interior fluid characterization was achieved by analyzing the propagation of the generated guided waves (for example, the lowest-order generalized antisymmetric Lamb wave, $a_0$) which is guided by the circumference of the container. The $a_0$ Lamb wave is in a class of guided waves which exhibit strong flexural vibrations near the resonance frequency of the container.

SUMMARY OF THE INVENTION

It is an object of the present invention to provide a non-contact apparatus and method for determining certain characteristics of fluids.

Another object of the invention is to provide an apparatus and method for determining certain characteristics of fluids without requiring nonlinear acoustic frequency down conversion to generate acoustic waves.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for non-contact characterization of a fluid in a container or a pipe, the container or pipe having a wall with an outer surface, hereof, includes: an air-coupled transmitting transducer disposed outside of the container or the pipe for generating ultrasonic waves approximately perpendicular to the outer surface of the wall at a chosen first distance therefrom; a sweep generator for exciting the air-coupled transmitting transducer at chosen frequencies in a selected frequency range, whereby resonant vibrations are generated in the fluid; an air-coupled receiving transducer disposed on the other side of the container or pipe from the transmitting transducer at a second chosen distance from the outer surface of the wall, for receiving the resonant vibrations emitted by the fluid perpendicular to the surface of the wall, the receiving transducer producing an electrical signal in response to the ultrasonic waves received thereby; a narrow-band tracking filter for receiving the electrical signal from the receiving transducer at the chosen frequencies in the selected frequency range and for generating a noise-filtered signal therefrom; and a signal processor for receiving the noise-filtered signal from the narrow-band tracking filter and producing a signal containing amplitude and phase information from the resonant ultrasonic vibrations in the frequency domain.

In another aspect of the present invention and in accordance with its objects and purposes, the method for non-contact characterization of a fluid in a container or a pipe, the container or pipe having a wall with an outer surface, hereof, includes the steps of: generating ultrasonic waves having a chosen frequency in a selected frequency range approximately perpendicular to the outer surface of the wall from a first chosen distance therefrom, whereby resonant ultrasonic vibrations are generated in the fluid; sweeping the generated ultrasonic waves over the selected frequency range; detecting resonant ultrasonic vibrations emitted by the outer surface of the wall of the pipe at a second chosen distance therefrom; producing a signal from the detected ultrasonic waves; and generating a narrow-band, noise-filtered signal at each frequency from the signal; whereby a signal containing amplitude and phase information from the resonant ultrasonic vibrations is generated in the frequency domain.

Benefits and advantages of the present invention include, but are not limited to, providing apparatus and method for non-contact method for characterizing fluids in pipes or containers having significantly greater signal-to-noise ratio than conventional time-of-flight measurements. Further, the large impedance mismatch between air and the walls of a pipe or container for ultrasound enables the apparatus of the present invention to provide isolated measurements without having to correct for transducer effects.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1 is a schematic representation of an embodiment of the apparatus of the present invention showing a hollow pipe having a transmitting transducer and a receiving transducer on opposite sides of the outside cylindrical surface thereof; a sweep generator for driving the transmitting transducer over a selected range of frequencies; low-pass filter circuitry for receiving and processing amplitude and phase information from the receiving transducer; a digital signal processor for receiving the output from the filter circuitry, processing amplitude and phase information from the signal processor in the frequency domain, and for performing a Fast Fourier Transform thereon to provide this information as a function of time; apparatus for controlling the electronic measurements; and apparatus for displaying and recording the resulting information, while

DETAILED DESCRIPTION OF THE INVENTION

Briefly, the present invention includes apparatus and method for non-contact ultrasonic determination of certain characteristics of liquids contained in containers or pipes. If a fluid-filled cavity, formed by the walls of two opposing piezoelectric transducers, is excited by sound, standing waves can be set up inside the fluid if the wavelength of the sound wave is an integral number of half-wavelengths. One transducer is used as the transmitter to which an electrical signal is applied to generate sound pressure waves inside the cavity, whereas the second transducer is used as a receiver to detect the standing waves, the so-called cavity resonances. A series of equidistant (in frequency) resonance (interference) peaks can be observed if the excitation signal is a periodic oscillatory waveform that is swept in frequency to cover a wide frequency range. The spacing between any two adjacent peaks is directly proportional to the sound speed in the liquid at the median frequency of the two peaks. The full-width-at-half-maximum of any resonance peak is related to the sound attenuation in the liquid at the peak frequency. Thus, by using a swept-sine wave excitation, both sound speed and sound attenuation for a fluid (liquid, mixture, emulsion, suspension, etc.) can be determined simultaneously over a wide frequency range.

The transducers need not be placed in contact with the fluid, the transducer system being located near the outside of the container wall, and measurements are made from the outside of the container. The fluid under investigation is contained in the space between the two walls, and the observed interference (standing wave) pattern has two superimposed components: in addition to the standing waves generated inside the liquid cavity, one observes standing wave patterns in the wall thickness of the container.

Air-coupled, high-power ultrasonic transducers for generating pressure waves, and for detecting these waves, were disposed at opposite sides of a container in which the fluid under investigation resides, and facing each other and the container. Containers may be fabricated from glass, metal, plastics, etc. The frequency range of the transducers was between 0.4 and 1.4 MHz, and the distance from the surface of the container between 0 and 5 cm. This permits a straight path for the sound through the container since, at these high frequencies, sound waves travel in a tightly confined beam. For example, the wavelength in air for 1 MHz sound wave is 0.34 mm.

The beam should impinge on the surface of a container (in particular, for flat surfaces such as a Starna cell) almost perpendicularly thereto. If the beam impinges at an angle to the surface other than about 90°, it becomes increasingly difficult to detect the received signal. Sound is transmitted directly through the container and into the liquid. There are no Lamb wave modes generated in the container walls since such waves would become severely attenuated by the liquid inside. Lamb waves also have a much smaller sound speed in container walls (a plate) than in the bulk form of the same material; as a result, if Lamb waves were generated there would be a delayed signal which can easily be identified with respect to those waves that travel directly through the wall. Such signals have not been observed from the embodiments of the apparatus of the present invention utilized. Additionally, there are no shear waves or Lamb wave modes possible in the liquid, since liquids only sustain longitudinal waves (pressure waves).

If the container has at least two parallel walls, and pressure waves are made to impinge on one of these walls, the opposite wall being used to detect waves generated in the fluid under investigation, strong resonances may be set up in the fluid, and resonances may be directly observed. By contrast, for non-parallel, but regular walls, resonances still are generated in the fluid, but their amplitudes are much smaller.

Further, as a result of the large impedance mismatch between air and the container wall, a large portion of the excitation sound energy is reflected, and a small fraction thereof enters the container wall. These waves propagate through the wall and into the fluid under investigation. A small amount of energy enters the opposite wall and is reradiated and detected by the detecting transducer which also suffers from losses due to impedance mismatch. Therefore, means for extracting small signal-to-noise ratio signals from the detected signal are provided.

In the present SFAI procedure, as will be described in more detail hereinbelow, measurements at each frequency between chosen start and stop frequencies are made through a narrow band (as an example, between about 100 Hz and 500 Hz) tracking filter restricting the received noise to a narrow, sliding frequency window throughout the entire frequency sweep range. In what follows, the term tracking filter will be used as representative of a filter which is effective at the various sine-wave frequencies employed and for which one embodiment is described in FIG. 1B hereof. There are many ways to implement such a tracking filter in practice and the electronics to do so are commercially available, such as a vector network analyzer. The swept frequency technique permits a 5 V excitation signal to generate high-quality measurements.

Although the frequency spectrum produced in many situations contained much noise after the large signal-to-noise ratio enhancement described hereinabove, upon transformation of the data into the time domain using a Fast Fourier Transform, the quality of the data was much improved. The time-domain data provided high-quality sound pulse transmission information from which time-of-flight of the acoustic waves through the fluid could readily be determined. Since the size of the container is easily measured, this led to an accurate determination of the speed of sound in the liquid. Further, the quality of the data was sufficiently good that multiple passes of the waves through the liquid could be measured, thereby providing sound attenuation information.

Pulse echo technology cannot provide adequate signal-to-noise ratio for such measurements. In accordance with the teachings of the present invention, however, it is possible to obtain the same time-domain information but from a frequency domain technique such that the noise bandwidth can be significantly reduced (orders of magnitude). Another advantage of using a time-domain procedure derived from a frequency sweep is the ability to achieve much higher signal-to-noise ratio information using much lower excitation voltages. Unlike the present invention, where measurements at each frequency between a start and stop frequency is made through a narrow band (~100 Hz) tracking filter restricting the received noise to a narrow, sliding frequency window throughout the entire frequency sweep range, the noise window for pulse-echo measurements is the equivalent of the entire bandwidth of the transmitted pulse. Thus, for a 1 MHz bandwidth measurement, the present swept frequency technique can provide a signal-to-noise ratio improvement of approximately 4 orders of magnitude (1 MHz/100 Hz) when comparing just the filter widths. In addition, the longer frequency sweep time (~10 s) to cover the entire frequency range as compared to a fast pulse that takes less than 1 μs provides additional signal-to-noise improvement. The total improvement can be as high as 80 db.

Figure 1A:
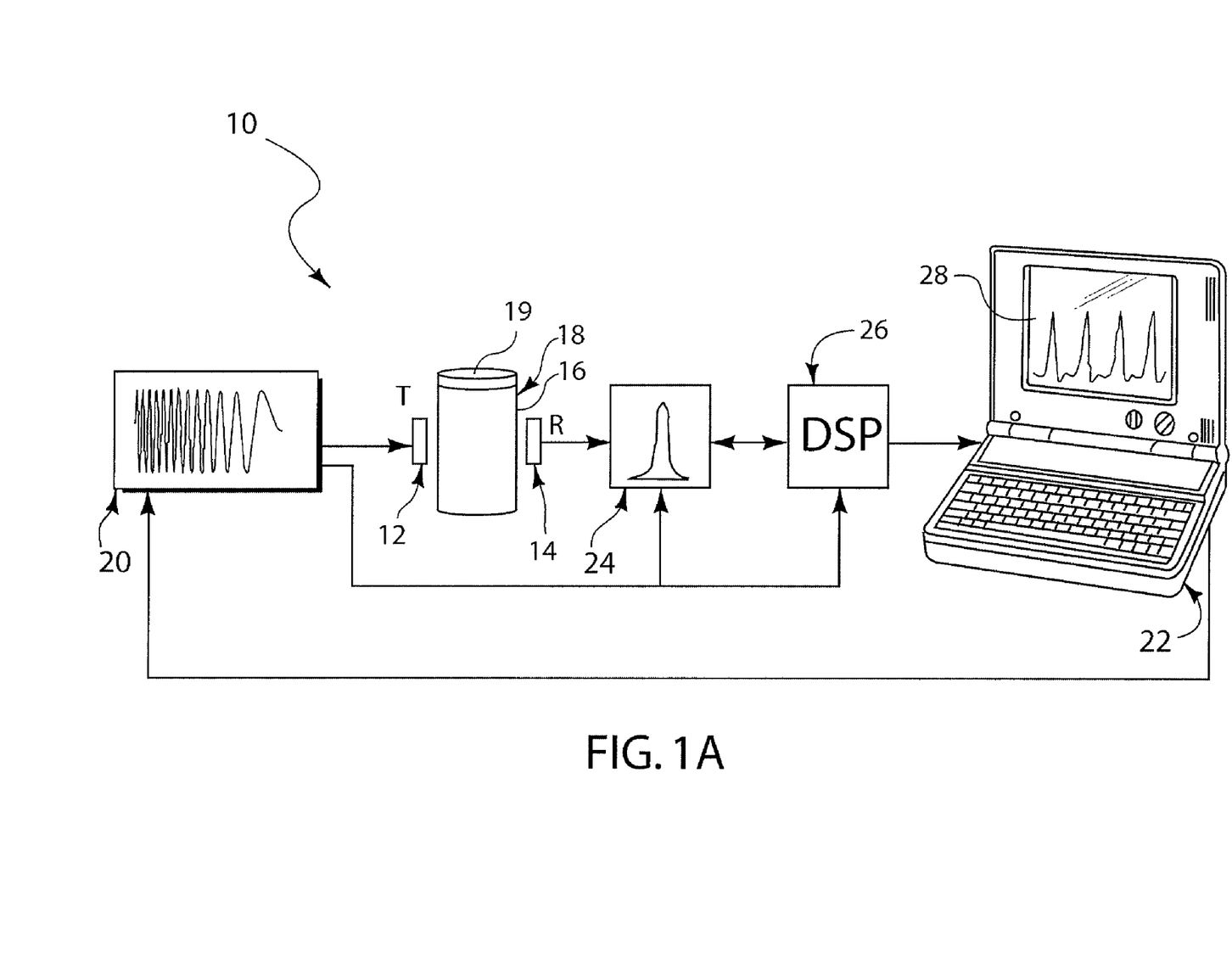
FIG. 1B shows the functional components of an embodiment of the electronic circuitry illustrated in FIG. 1A hereof.

Reference will now be made in detail to the present embodiments of the invention, examples of which are illustrated in the accompanying drawings. In the FIGURES, similar structure will be identified using identical reference characters. Turning now to FIG. 1A, a schematic representation of one embodiment, 10, of the swept frequency apparatus of the present invention is illustrated. Transmitting transducer, 12, and receiving transducer, 14, are gas matrix air-coupled transducers obtained from Ultran Laboratories in Pennsylvania. Transducers 12 and 14 are broadband transducers (frequency range: 400 kHz-1.4 MHz) having high power output and very sensitive reception, and are intended to be illustrated in FIG. 1 as being disposed between about 2.5 cm and 5 cm from the outside wall surface, 16, of container, 18 in transmission mode. Shown also is container cap, 19, adapted for rendering container 18 fluid-tight. Sweep generator, 20, controlled by microprocessor, 22, drives transmitting transducer 12 through a selected frequency range of sine wave voltages (~5V amplitude). Transmitted and radiated signals received by receiving transducer 14, are directed through narrow-bandpass filter circuitry, 24, to digital signal processor electronics, 26, where it is processed, including conversion of the frequency spectrum to the time domain by FFT (Fast Fourier Transform), stored, and displayed by display apparatus 28. DSP 26 may also carry out various math operations to process the data further, if desired.

To recover information in a frequency sweep measurement one needs to restrict the noise to a narrow bandwidth. Further, amplitude and phase measurements must be made within this narrow bandwidth. A complex Fourier transform using both amplitude and phase values is then made to recover the time-domain data with very high signal-to-noise ratio. In principle, the measurements are made through a narrow band-pass filter that effectively tracks the frequency sweep.

Figure 1B:
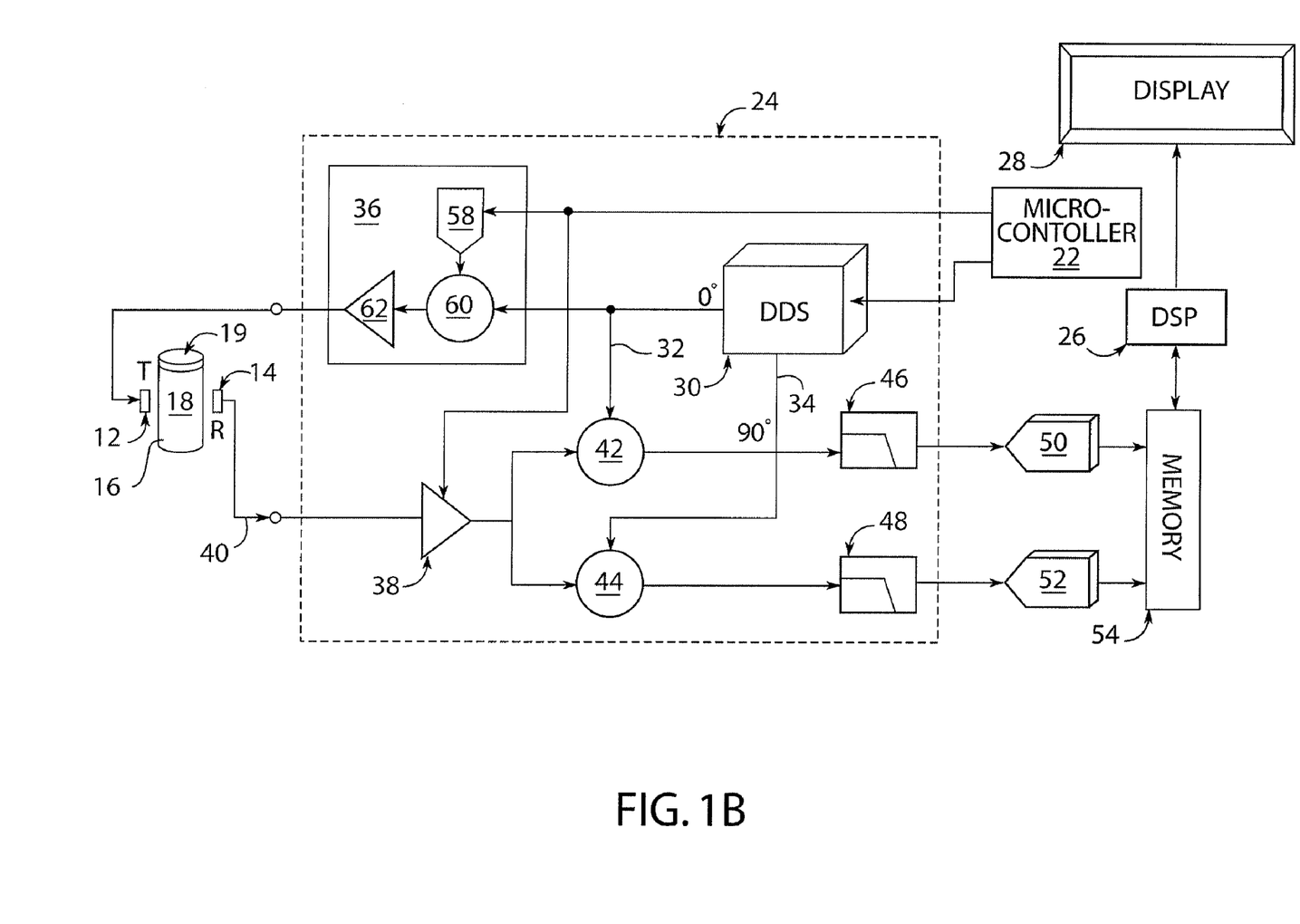

Turning now to FIG. 1B, which further describes narrow band pass filter 24, and control electronics 22, a signal (sine-wave) is applied to transmitter transducer and picking up a signal using a receiver transducer. The received signal has traveled a certain distance in the container walls and the fluid which generates a time delay or phase delay relative to the impressed signal. Additionally, the signal may also lose some energy during this propagation and so its amplitude may vary. The received signal is compared with the original input signal (at 0°) and at its phase shifted value of 90° degrees which is known as signals in quadrature. The received signal is multiplied with signals in quadrature and the resultant signals passed through a low pass filters to remove extraneous higher frequency signals. The cutoff frequency of the low-pass filter is chosen at a desired fixed frequency, such as 100 Hz for all sweep frequencies, the system generating in effect a tracking narrow band-pass filter having a desired bandwidth, but using fixed, narrow low band-pass filters.

As stated hereinabove, the sweep measurement requires the simultaneous determination of both phase and amplitude of the received signal within a narrow frequency band. This measurement needs to be made at every frequency as the frequency is varied between selected limits (low and high values). The circuitry used for this is described in FIG. 1B.

Micro-controller/processor 22 controls direct digital synthesizer (DDS), 30, having quadrature output (sine wave having a desired frequency and 0°, 32, and 90°, 34, of phase relationship with one another), programmable gain amplifier, 36, for driving transmitter transducer 12, in pipe 18 and variable gain amplifier, 38, for amplifying received signal, 40, from receiver transducer 14. Two double-balanced mixers, 42 and 44, and two low-pass filters, 46 and 48, respectively, mix the signals from DDS 30 with the output from amplifier 38 and filter the high frequencies. The filtered signals are directed to analog-to-digital converters (ADC), 50 and 52, respectively and stored in memory, 54. DSP 26 processes the stored signals which may be displayed by display 28.

Microcontroller 22 is programmed to communicate with DDS 30 to generate two sine waves having the same frequency and a 900 phase difference between the two outputs. The 0° signal is directed to programmable gain amplifier 36, the gain of which is derived from a gain value (DC voltage signal) from 8-bit digital-to-analog converter (DAC), 58, and is then multiplied, 60, with the sine wave signal from DDS 30, to produce a desired signal amplitude. This signal goes through power amplifier, 62, to drive transmitter (T) transducer 12. The signal from receiver (R) transducer 14 is amplified by a variable gain (user selectable gain) amplifier 38 and directed to simultaneously to mixers 42 and 44. Mixers 42 and 44 also receive in quadrature sine wave signals 32 and 34, respectively, and the resulting outputs are low-pass filtered, 46 and 48, respectively. The cut-off frequency of low pass filters 46 and 48 (for example, 100 Hz) determines the narrow-frequency bandwidth of the measurement at a given frequency. The output of the low-pass filters are the Real (0°) and Imaginary (90°) components of received signal 40. The output of low-pass filters 46 and 48 are then digitized by ADCs 50 and 52, respectively, converted to gain and phase values by DSP 26, and stored in memory. The resulting frequency spectrum may be displayed on display device 28. The DSP system may also convert the frequency spectrum to the time domain by FFT which may also be displayed. As stated, DSP 26 may perform various math operations to process the data further, as desired.

Typically, the frequency sweeps are performed with between 1024 and 8192 frequency steps between the two chosen frequency limits depending on the transducers used and the sample being tested. The described apparatus has the capability to produce and process a frequency range of 100 Hz to 10 MHz, and the number of frequency steps can be as large as 64,000 steps. Typical sweep times vary from 2 s to 10 s for a given measurement, but the electronics is not limited to that. The cut-off frequency of the low-pass filters can be increased to obtain higher speed, if desired. The excitation voltage for the transmitter transducer is typically less than 10 V (this low voltage protects the transducers from degradation over time), although the apparatus has the capability of generating higher voltages.

As stated, the electronics behave as a narrow band (~100 Hz) tracking band-pass filter. This means only the signal within that 100 Hz bandwidth (this value can be different than 100 Hz, and the exact value is not critical) is detected, thereby improving the signal-to-noise ratio immensely. The processing gain achieved by this frequency sweep approach is better than 80 dB. The electronics described permits measurement of both the amplitude and the phase of the received signal as compared to the transmitted signal as a function of frequency. However, in a significant number of situations, signal processing with the improvement in signal-to-noise ratio by 80 dB, the measured spectrum of the transmitted sound through the container as a function of frequency may appear like a noise spectrum in cases where the container walls are not parallel. However, this noisy spectrum contains information regarding how the sound propagates through the fluid inside the container and how each frequency behaves as it interacts with the fluid medium.

Transforming this frequency spectrum to the time domain using complex (real and imaginary) Fast Fourier Transform of the data, permits multiple time domain echoes to be clearly seen, thereby permitting the determination of sound attenuation as the sound waves traverse the container. Contact SFAI has demonstrated that sound speed and sound attenuation can be used to identify and characterize various fluids and chemicals which is shown to be possible using the non-contact transducers in accordance with the present invention.

Figure 2A:
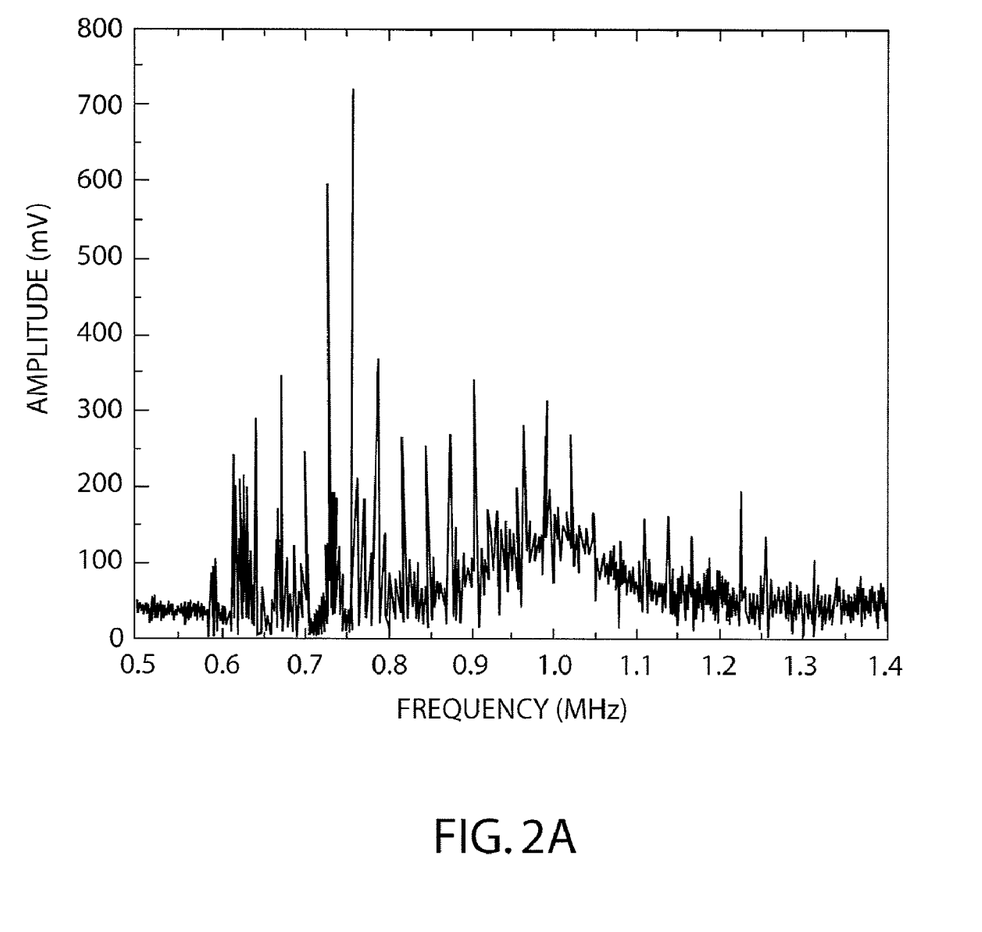
FIG. 2A is a graph of the amplitude of the swept frequency acoustic interference (SFAI) signal received from an air-coupled transducer from an optical glass cell from Starna, Inc. containing Isopropanol as a function of frequency.
Figure 2B:
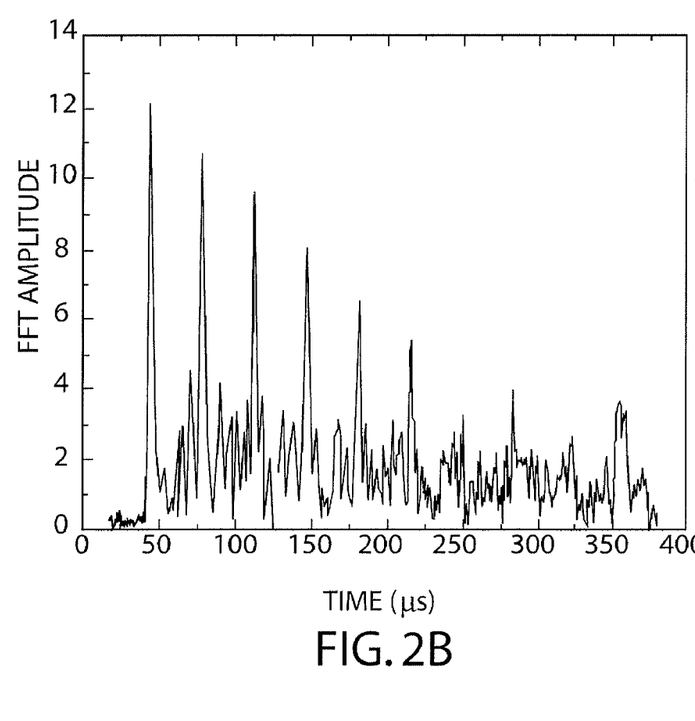
FIG. 2B is a graph of the Fast Fourier Transformed amplitude and phase data of FIG. 2A hereof as a function of time.
Figure 2C:
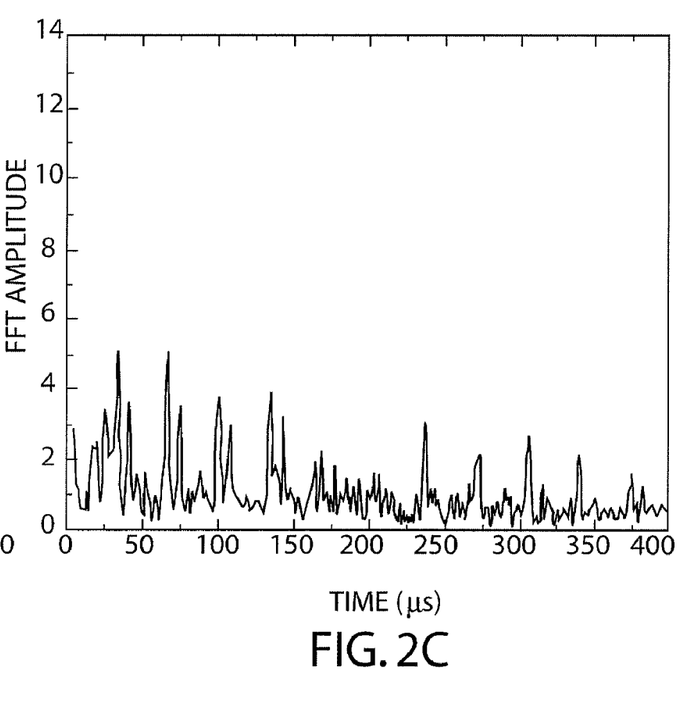
FIG. 2C is a graph of the Fast Fourier Transformed amplitude data only, without including the phase information.

FIG. 2A is a graph of the amplitude of the swept frequency acoustic interference (SFAI) signal received from an air-coupled transducer from a Starna Cell containing Isopropanol as a function of frequency; FIG. 2B is a graph of the Fast Fourier Transformed amplitude and phase data of FIG. 2A hereof as a function of time; and FIG. 2C is a graph of the Fast Fourier Transformed amplitude data only, without including the phase information.

Figure 3A:
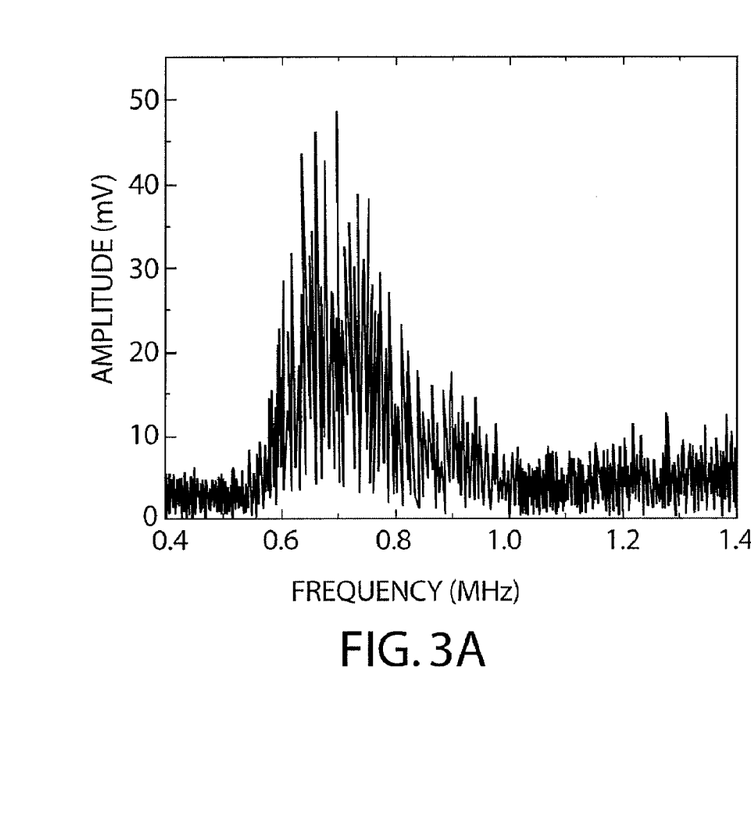
FIG. 3A is a graph of the non-contact amplitude as a function of frequency for a full plastic soft drink bottle.
Figure 3B:
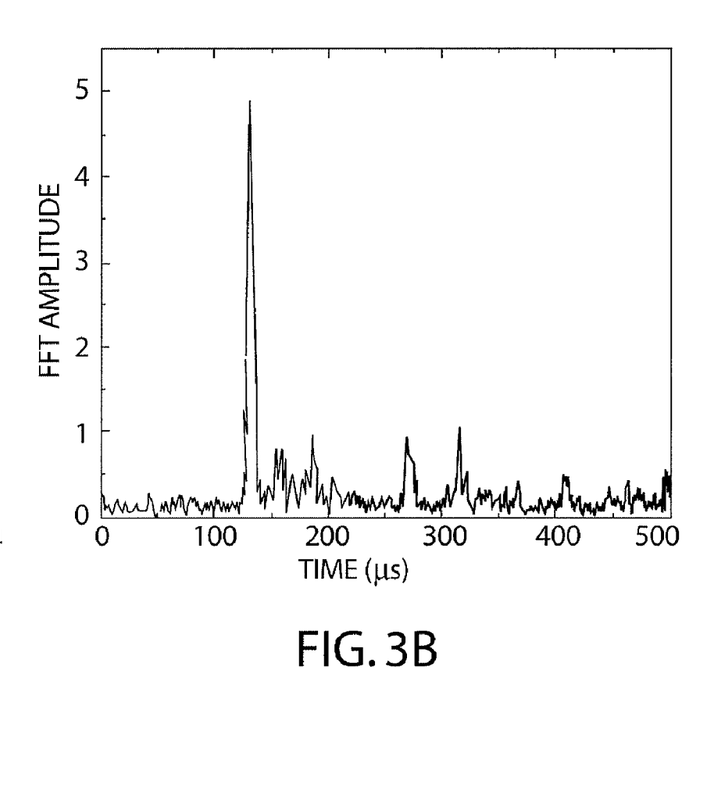
FIG. 3B is a graph of the Fast Fourier Transformed amplitude and phase data of FIG. 3A.

FIG. 3A is a graph of the non-contact amplitude as a function of frequency for a full plastic soft drink bottle; and FIG. 3B is a graph of the Fast Fourier Transformed amplitude and phase data of FIG. 3A.

Figure 4A:
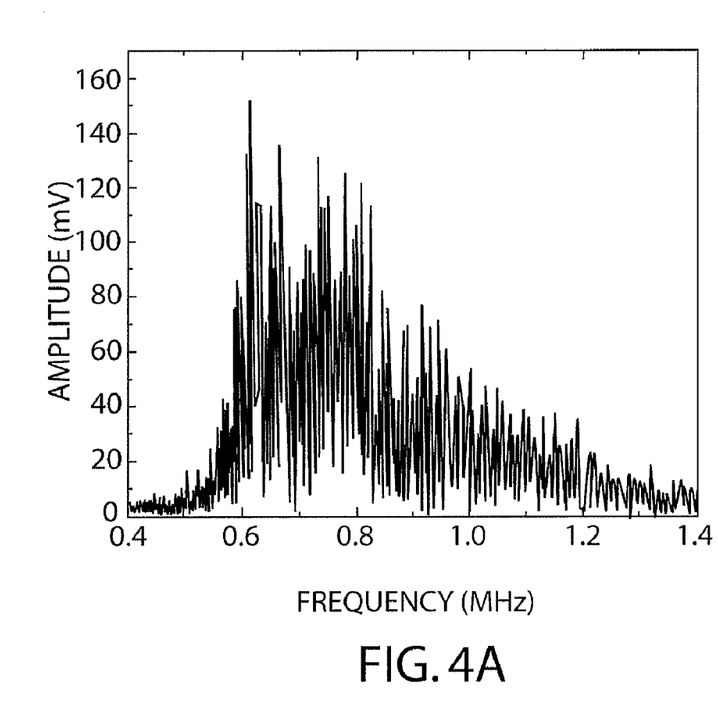
FIG. 4A is a graph of the non-contact amplitude as a function of frequency for a full soft drink can.
Figure 4B:
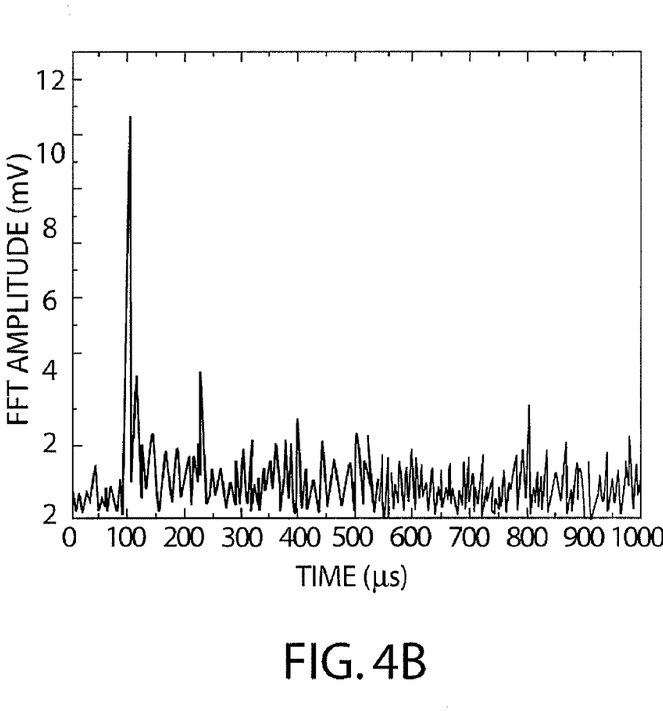
FIG. 4B is a graph of the Fast Fourier Transformed amplitude and phase data of FIG. 4A.

FIG. 4A is a graph of the non-contact amplitude as a function of frequency for a full soft drink can; and FIG. 4B is a graph of the Fast Fourier Transformed amplitude and phase data of FIG. 4A.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for non-contact characterization of a fluid in a container or a pipe, said container or said pipe having a wall having an outer surface, comprising in combination:

an air-coupled transmitting transducer disposed outside of said container or said pipe for generating ultrasonic waves approximately perpendicular to the outer surface of the wall at a chosen first distance therefrom;

a sweep generator for exciting said air-coupled transmitting transducer at chosen frequencies in a selected frequency range, whereby resonant vibrations are generated in the fluid;

an air-coupled receiving transducer disposed in any configuration on the other side of said container or said pipe from said transmitting transducer at a second chosen distance from the outer surface of the wall, for receiving said resonant vibrations emitted by said fluid and perpendicular to the outer surface of the wall, said receiving transducer producing an electrical signal in response to the ultrasonic waves received thereby;

a narrow-band tracking filter for receiving the electrical signal from said receiving transducer at the chosen frequencies in the selected frequency range and for generating a noise-filtered signal therefrom;

a signal processor for receiving the noise-filtered signal from said narrow-band tracking filter and producing a signal containing simultaneous amplitude and phase information from the ultrasonic waves in the frequency domain; and circuitry for receiving the signal from said signal processor in the frequency domain and transforming the signal into the time domain by Fast Fourier Transform.

2. The non-contact characterization apparatus of claim 1, wherein the selected frequency range is between 0.4 and 1400 kHz.

3. The non-contact characterization apparatus of claim 1, wherein the first chosen distance from an inner surface of the wall of said container or said pipe, and the second chosen distance from the inner surface of the wall of said container or said pipe, are greater than 1 cm.

4. The non-contact characterization apparatus of claim 1, wherein the outer surface has two parallel walls, said transmitting transducer being perpendicular to one of the parallel walls and said receiving transducer being perpendicular to the other of the parallel walls.

5. A method for non-contact characterization of a fluid in a container or a pipe, the container or pipe having a wall with an outer surface, comprising the steps of:

generating ultrasonic waves having a chosen frequency in a selected frequency range approximately perpendicular to the outer surface of the wall from a first chosen distance therefrom, whereby resonant ultrasonic vibrations are generated in said fluid;

sweeping the generated ultrasonic waves over the selected frequency range to obtain simultaneous amplitude and phase measurements;

detecting the resonant ultrasonic vibrations emitted perpendicular to the outer surface of the wall of the container or the pipe at a second chosen distance therefrom;

producing a signal from the detected ultrasonic vibrations;

generating a narrow-band, noise-filtered signal at each frequency from the signal; whereby a signal containing amplitude and phase information from the resonant ultrasonic vibrations is generated in the frequency domain; and transforming the signal containing amplitude and phase information into the time domain by Fast Fourier Transform.

6. The non-contact characterization method of claim 5, wherein the selected frequency range is between 400 and 1400 kHz.

7. The non-contact characterization method of claim 5, wherein the first chosen distance from the surface of said container or said pipe and the second chosen distance from the surface of said container or said pipe, are greater than 1 cm.

8. The non-contact characterization method of claim 5, wherein said step of generating ultrasonic waves having a chosen frequency is achieved using an air-coupled transmitting transducer disposed outside of the container or the pipe and excited by a sweep generator, and said step of detecting ultrasonic waves emitted by the fluid is achieved using an air-coupled receiving transducer disposed outside of the container or the pipe on the opposite side of the container or the pipe from the transmitting transducer.

9. The non-contact characterization method of claim 8, wherein the outer surface has two parallel walls, the transmitting transducer being perpendicular to one of the parallel walls and the receiving transducer being perpendicular to the other of the parallel walls.

* * * * *